United States Patent
Kuslich et al.

[11] Patent Number: 5,989,256
[45] Date of Patent: Nov. 23, 1999

[54] BONE FIXATION CABLE FERRULE

[75] Inventors: Stephen D. Kuslich, Stillwater, Minn.; Francis Peterson, Prescott, Wis.

[73] Assignee: Spineology, Inc., Stillwater, Minn.

[21] Appl. No.: 09/232,962

[22] Filed: Jan. 19, 1999

[51] Int. Cl.[6] .................................................. A61B 17/56
[52] U.S. Cl. ............................... 606/74; 606/61; 606/73; 606/103
[58] Field of Search ................................. 606/61, 72, 73, 606/74, 103; D4/199; 411/393, 395; 403/362; 623/13, 17

[56] References Cited

U.S. PATENT DOCUMENTS

| | | |
|---|---|---|
| 4,047,523 | 9/1977 | Hall . |
| 4,146,022 | 3/1979 | Johnson et al. . |
| 4,590,929 | 5/1986 | Klein . |
| 4,790,303 | 12/1998 | Steffee . |
| 4,828,562 | 5/1989 | Kenna . |
| 4,966,142 | 10/1990 | Meinershagen . |
| 5,108,397 | 4/1992 | White . |
| 5,151,104 | 9/1992 | Kenna . |
| 5,250,055 | 10/1993 | Moore et al. . |
| 5,304,178 | 4/1994 | Stahurski . |
| 5,354,299 | 10/1994 | Coleman ................................... 606/73 |
| 5,395,374 | 3/1995 | Miller et al. . |
| 5,571,139 | 11/1996 | Jenkins, Jr. ............................. 606/232 |
| 5,702,397 | 12/1997 | Goble et al. ............................. 606/72 |
| 5,797,915 | 8/1998 | Pierson, III et al. . |
| 5,797,916 | 12/1998 | McDowell . |
| 5,810,825 | 9/1998 | Huebner . |

*Primary Examiner*—Michael Buiz
*Assistant Examiner*—Julian W. Woo
*Attorney, Agent, or Firm*—Vidas, Arrett & Steinkraus, P.A.

[57] ABSTRACT

A ferrule for insertion in an opening cut through a vertebral spinous process functions as a guide for a connecting cable, preventing cutting into the bone by the cable and protecting the cable from breakage.

7 Claims, 4 Drawing Sheets

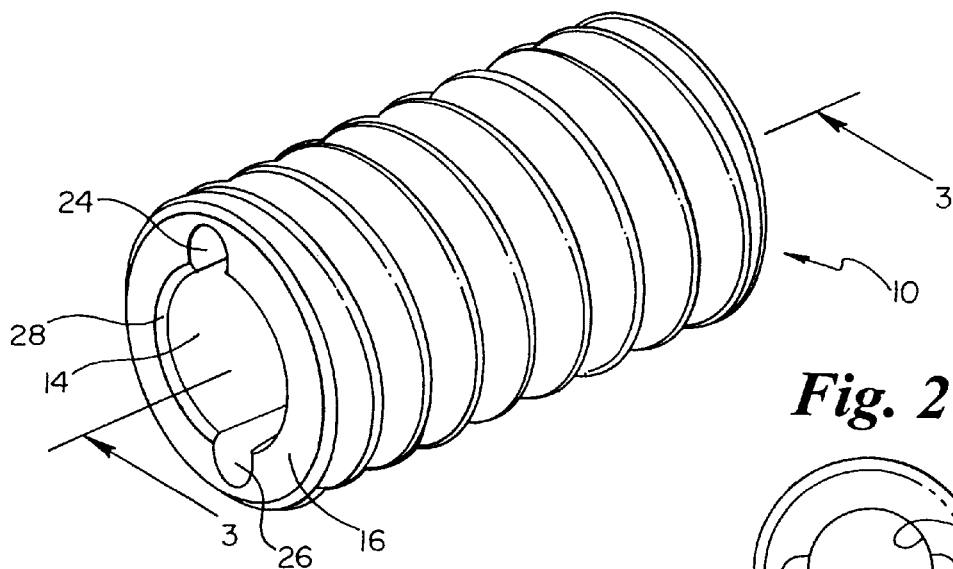
Fig. 1
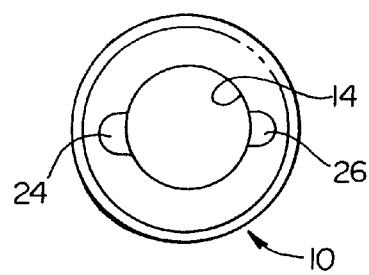
Fig. 2
Fig. 3
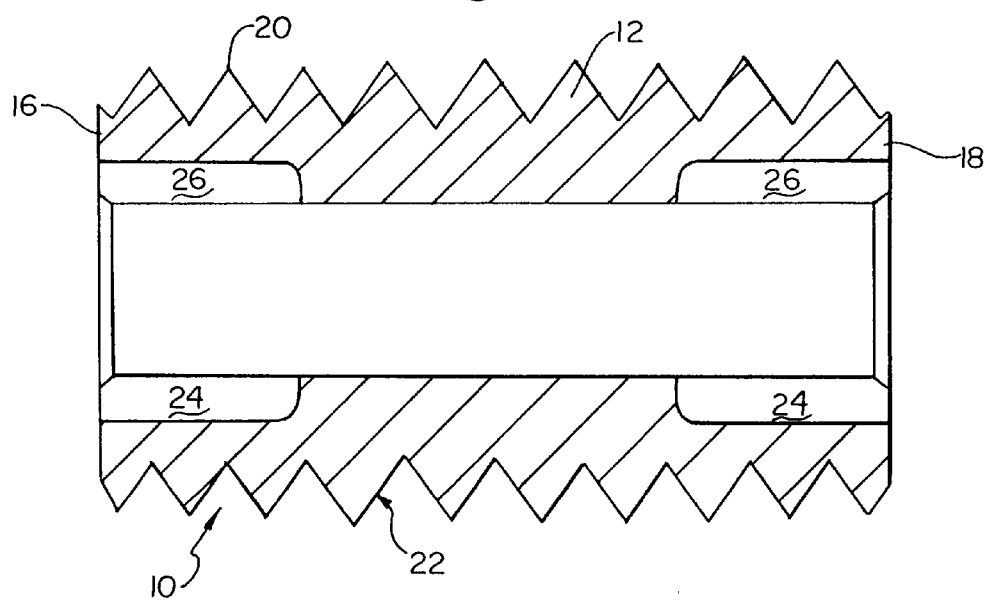

BONE FIXATION CABLE FERRULE

BACKGROUND OF THE INVENTION

1. Field of the Invention

This invention relates to bone fixation systems which use wire or cable to lock two or more bone segments together, including the back, or spinous process of adjacent vertebrae together or locking a spinal bone to another fixation device. More particularly, the invention relates to a ferrule for protecting the bone from being cut by the cable.

2. Description of the Related Art

In spinal surgery, the surgeon often locks adjacent vertebrae together. In some cases, the surgeon additionally locks adjacent vertebrae together through the spinous process by a cable around bony edges or through holes drilled in the bone.

Stahurski, U.S. Pat. No. 5,304,178, shows a sublaminar wire for connecting a corrective device to the spinal column. A center portion is positionable under the lamina of a vertebra and has a varying cross-sectional area. The inventor notes that wire may tear through the lamina due to their small diameters. Howland, U.S. Pat. No. 5,030,220, discloses a spinal fixation system having pedicle screws and rods as well as sublaminar wires with a wire protector to protect the rod/wire interface. The wires are passed under the lamina and over the wire protectors which encase the serrated rod.

Klein, U.S. Pat. No. 4,590,929, describes the use of twisted wire connections for connecting bone fragments. He notes that apertures in the bone may cause breakage of the wires and reduces wire breakage by cutting the bone at the breakage point.

Johnson et al., U.S. Pat. No. 4,146,022, discloses a method for fixing bone fractures by wire using an implant embedded in the cortex of a bone. The implant has a cylindrical body portion and a circular bore through which a wire may be passed. That device uses spikes into the bone to provide a raised member that prevents the wire from cutting into the bone.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists.

SUMMARY OF THE INVENTION

The invention provides a ferrule which guides and protects both the bone and the cable when adjacent vertebra are tied together with cable. A ferrule is positioned into openings formed in the spinous process of each vertebra. The cable is then threaded though the bores of the ferrules and tightened as is known in the art to properly connect the vertebra together. The ferrules have a substantially smooth internal bore which opens at both ends to an outwardly flaring or radiused opening which has opposing slots which allow placement of the ferrules into the bone opening with a screwdriver or similar tool.

The inventive ferrule would also work well as a tension band protector for any procedure that reconnects bone fragments. The ferrule may also be used to lock bone to tendons or ligaments, as in tendon rips requiring reattachment to the patella.

BRIEF DESCRIPTION OF THE DRAWINGS

A detailed description of the invention is hereafter described with specific reference being made to the drawings in which:

FIG. 1 is a perspective view of the externally threaded ferrule;

FIG. 2 is an end view of the ferrule showing its hollow bore;

FIG. 3 is a cross-sectional view of the ferrule of FIG. 1;

DESCRIPTION OF THE PREFERRED EMBODIMENTS

Figure 5:
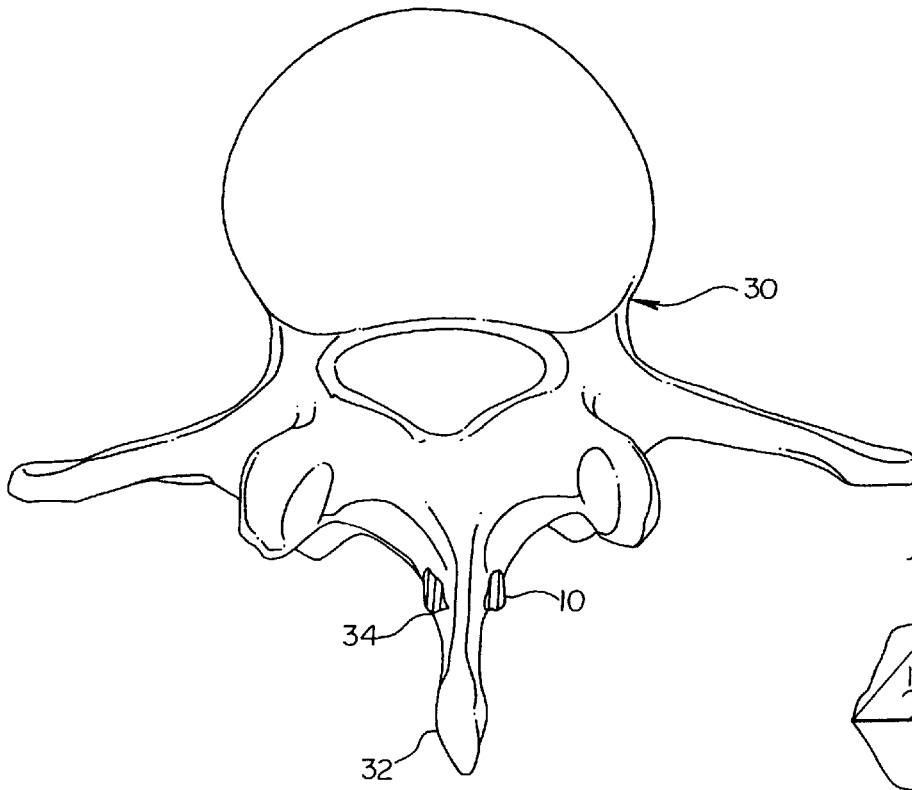
FIG. 5 is a top view of a vertebra showing a ferrule through the spinous process.

With reference to the Figures it will be seen that ferrule 10 has a cylindrical main body 12, a hollow bore 14 extending between its distal end 16 and proximal end 18. Ferrule 10 includes bone engaging threads 20 on its exterior surface 22. Although threads are shown, any surface modification which would help to prevent movement of the ferrule when inserted into a hole cut into the bone may function well. Therefore, the use of the term "threads" herein is not limited to conventional threads but includes surface roughening and other techniques such as used in the hip implant field. The phrase "bone engagement members" as used herein includes the previously described "threads" and surface treatments that promote bone ingrowth and resists back and forth movement of the device in a hole cut in bone..

Figure 4:
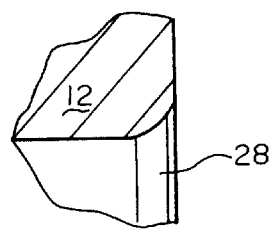
FIG. 4 is an enlarged, partial cross-sectional view of an end of a ferrule of FIG. 3 showing the radius of the ends.

As best shown in FIGS. 3 and 4, the hollow bore 14 includes a pair of opposing slots 24, 26 which pass down into the bore 14. The slots 24, 26 allow a screwdriver or similar tool to fit within the ferrule so the ferrule may be threaded into an opening cut into bone. The slots may be on one or on both ends of the ferrule. If placed on only one end, the slots may indicate the direction of the threads to the surgeon. Alternatively, the slots may be on both ends so the surgeon could adjust the position of the ferrule in the spinous process by applying a tool to either end. Use of the term "opposing slots" is intended to cover the use of a slotted screwdriver, but is also intended to cover phillips screwdriver and other conventional driving heads.

Figure 6:
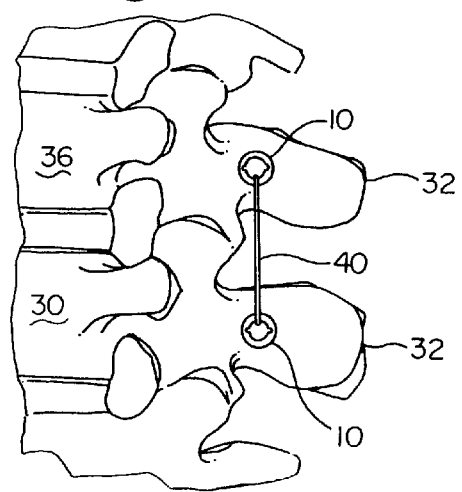
FIG. 6 is a side view of adjacent vertebra cabled together with the cable passing through ferrules of the invention placed into the spinous process.

FIG. 5 shows a typical vertebra 30 which includes a spinous process 32 through which an opening 34 has been cut and a ferrule 10 has been inserted. In FIG. 6, two adjacent vertebra 30, 36 are shown with ferrules 10 in each spinous process 32 and a cable 40 passes through each ferrule 10. The cable 40 is tightened as needed by the surgeon and the ends of the cable are tied off in any of the currently accepted methods. As a result of the ferrules of the invention, the cable 40 cannot cut in a sawing action into the bone of the spinous process. Use of the term "cable" herein is meant to cover cables, wires, tapes, bands and the like used in surgery to tie together vertebrae. The cable may be metal or non-metal and is meant to fully cover any material used as a cable or cable equivalent. Preferably, ends 16 and 18 of ferrule 10 have a radius 28 into the bore 14 to minimize strain on the wire 40 as it bends into the bore 14. Note that the ferrule of the invention has been described as being generally cylindrical. That term as used herein includes oval shapes, as the benefits of the invention may be found in any ferrule which may be readily positioned and held in an opening formed in bone so long as the ferrule may be inserted into the opening where it will stay in place and guide the cable to prevent sawing of the bone.

Figure 7:
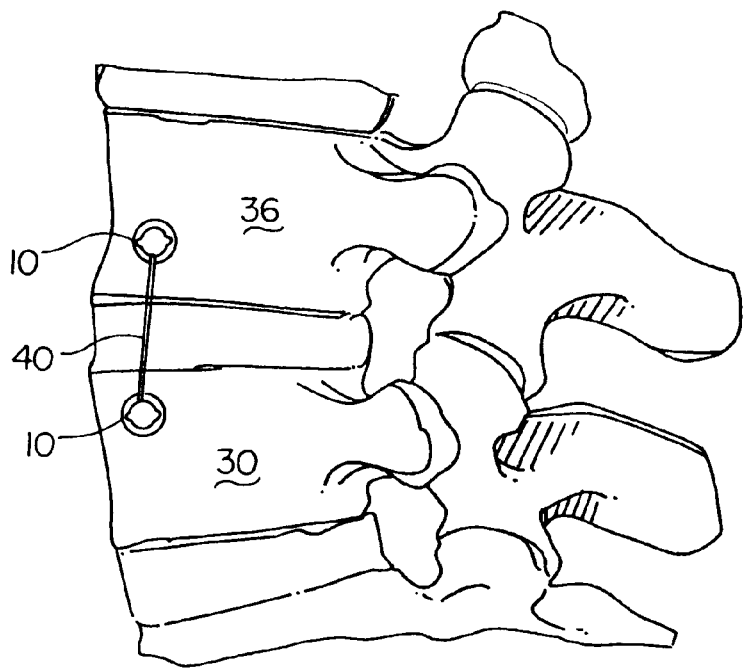
FIG. 7 shows a side view of adjacent vertebra cabled together through the bodies of the vertebrae.
Figure 8:
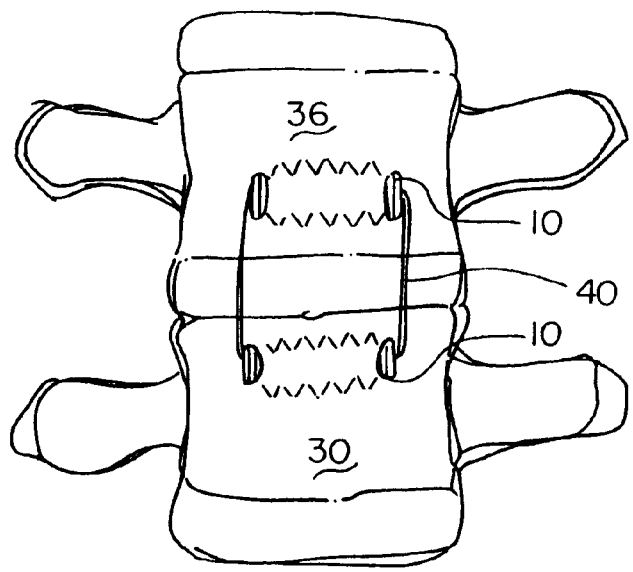
FIG. 8 shows an anterior view of the cabling of FIG. 6.
Figure 11:
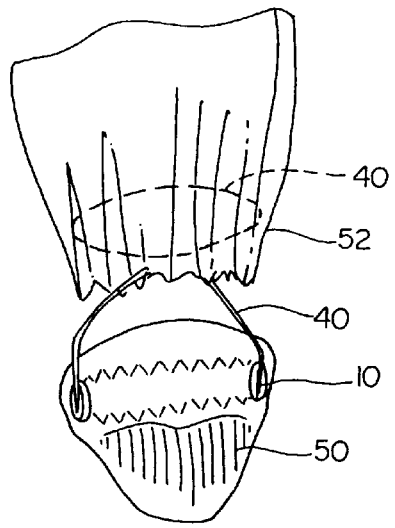
FIG. 11 shows a patellar tendon repair with the ferrule of the invention.
Figure 9:
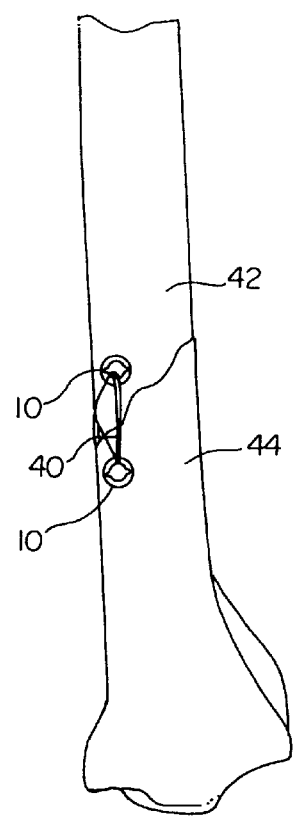
FIG. 9 shows connection of two pieces in a long bone such as a femur.
Figure 10:
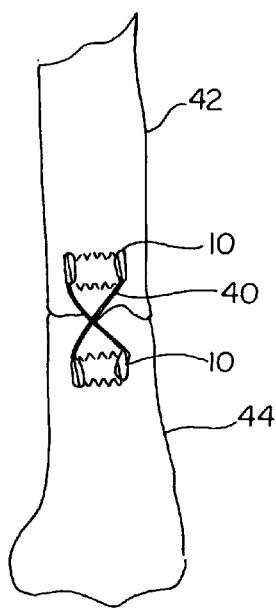
FIG. 10 shows a front view of the connection of bone in FIG. 9.
Figure 12:
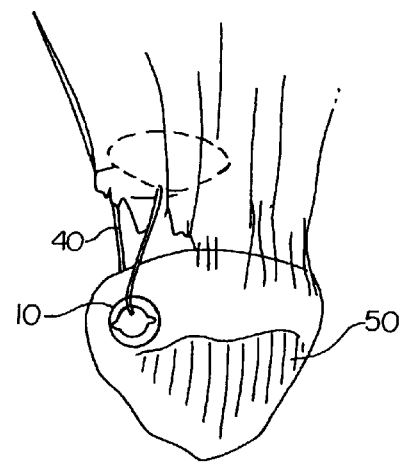
FIG. 12 shows a torn patellar tendon employing the ferrule of the invention.

FIGS. 7 and 8 show that the ferrules 10 of the invention may be used to protect and guide cables connecting adjacent vertebrae through their bodies, and not simply involving the spinous process. FIGS. 9 and 10 show repair of a broken long bone, such as a femur with bone fragments 42, 44 being wired together with cable 40 and a pair of ferrules 10. Finally, FIGS. 11 and 12 show that the ferrule may protect bone in a knee in re-connecting or repairing the connection between the patella 50 and the tendon 52. Note that the advantages of the invention are obtained by any connection process between a bone and another body part, including another bone, ligament or tendon since the ferrule will limit damage to the bone from the cable.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A system for protecting a vertebral spinous process from being cut when cabling together spinous process in a patient in need of such cabling, the system comprising:
   (a) a pair of ferrules, each of said ferrules including:
      a generally cylindrical, hollow main body having a proximal and a distal end, said main body having an exterior and interior surface;
      a bore extending through said main body through said distal and proximal ends;
      at least one of said proximal and distal ends of each said ferrule including a tool-engaging member leading into the bore of each said ferrule;
      said ferrule including bone engagement members on said exterior surface of said main body; and
   (b) a cable extending through the bore of said ferrules, said cable forming a closed loop.

2. The apparatus of claim 1 wherein said bone engagement members are threads.

3. The apparatus of claim 2 wherein said main body has a radiused entry into said bore to minimize strain on a cable passing across and end into said bore.

4. A system for protecting a bone from being cut when cabling together a bone to a bone in a patient in need of such cabling, the system comprising:
   (a) a pair of ferrules, each of said ferrules including:
      a generally cylindrical, hollow main body having a proximal and a distal end, said main body having an exterior and interior surface;
      a bore extending through said main body through said distal and proximal ends;
      at least one of said proximal and distal ends of each said ferrule including a tool-engaging member leading into the bore of each said ferrule;
      said ferrule including bone engagement members on said exterior surface of said main body; and
   (b) a cable extending through the bore of said ferrules, said cable forming a closed loop.

5. A method for connecting adjacent vertebra in a patient in need of such treatment comprising the steps of:
   (a) forming a hole through the spinous process in adjacent vertebra;
   (b) inserting a hollow, externally threaded ferrule into each hole thus formed, each said ferrule including a bore extending from a proximal to a distal end, at least one of said proximal and distal ends of said ferrule including a pair of opposed, tool-engaging slots leading into the bore of said ferrule;
   (c) threading a cable through the bores of said ferrules;
   (d) connecting the ends of said cable such that tension is applied to the adjacent vertebra.

6. A method for connecting bone to bone in a patient in need of such treatment comprising the steps of:
   (a) forming a hole in each bone to be joined;
   (b) inserting a hollow, externally threaded ferrule into each hole thus formed, each said ferrule including a bore extending from a proximal to a distal end, at least one of said proximal and distal ends of said ferrule including a tool-engaging member leading into the bore of said ferrule;
   (c) threading a cable through the bores of said ferrules;
   (d) connecting the ends of said cable such that tension is applied to each bone.

7. An apparatus for protecting bone from being cut when cabling together a bone to a bone in a patient in need of such cabling, the apparatus comprising:
   (a) a generally cylindrical, hollow ferrule having a main body having a proximal and a distal end, said main body having an exterior and interior surface, said main body including a radiused entry at both proximal and distal ends to minimize strain on a cable passing transversely across said ends;
   (b) a bore extending through said main body through said distal and proximal ends;
   (c) at least one of said proximal and distal ends of said ferrule including a tool-engaging member leading into the bore of said ferrule; and
   (d) said ferrule including bone engagement members on said exterior surface of said main body.

* * * * *